(12) United States Patent
Copa et al.

(10) Patent No.: US 8,066,725 B2
(45) Date of Patent: Nov. 29, 2011

(54) ANASTOMOSIS DEVICE HAVING IMPROVED SAFETY FEATURES

(75) Inventors: Vincent G. Copa, Minnetonka, MN (US); Sidney F. Hauschild, St. Paul, MN (US); Suranjan Roychowdhury, Plymouth, MN (US); Kory P. Hamel, Bloomington, MN (US); Robert L. Rykhus, Edina, MN (US); Jay Soderberg, Plymouth, MN (US)

(73) Assignee: AMS Research Corporation, Minnetonka, MN (US)

( * ) Notice: Subject to any disclaimer, the term of this patent is extended or adjusted under 35 U.S.C. 154(b) by 946 days.

(21) Appl. No.: 11/873,888

(22) Filed: Oct. 17, 2007

(65) Prior Publication Data
US 2008/0097493 A1    Apr. 24, 2008

Related U.S. Application Data

(60) Provisional application No. 60/829,803, filed on Oct. 17, 2006.

(51) Int. Cl.
*A61B 17/08* (2006.01)
(52) U.S. Cl. ........................................ 606/153; 604/544
(58) Field of Classification Search .................. 606/152, 606/153, 198, 151, 154, 156; 600/36; 604/544; 623/1.23
See application file for complete search history.

(56) References Cited

U.S. PATENT DOCUMENTS

| | | | |
|---|---|---|---|
| 4,701,162 A | 10/1987 | Rosenberg | |
| 4,705,502 A | 11/1987 | Patel | |
| 4,792,330 A | 12/1988 | Lazarus | |
| 4,848,367 A | 7/1989 | Avant et al. | |
| 4,873,977 A | 10/1989 | Avant et al. | |
| 4,909,785 A | 3/1990 | Burton et al. | |
| 4,911,164 A | 3/1990 | Roth | |
| 4,932,956 A | 6/1990 | Reddy et al. | |
| 5,047,039 A | 9/1991 | Avant et al. | |

(Continued)

FOREIGN PATENT DOCUMENTS
WO      WO 92/04869    4/1992

(Continued)

OTHER PUBLICATIONS

Igel et al., "Comparison of Techniques for Vesicourethral Anastomosis: Simple Direct Versus Modified Vest Traction Sutures," Urology, vol. XXXI, No. 6, pp. 474-477 (Jun. 1988).

(Continued)

*Primary Examiner* — Victor Nguyen
(74) *Attorney, Agent, or Firm* — Kimberly K. Baxter; Gregory L. Koeller (57) ABSTRACT

An anastomosis device providing increased functionality, reliability and safety through the use of designs addressing potential puncture of an inflation balloon being used to hold and approximate tissue. The anastomosis device can include bladder retention structures configured to engage and retain tissue without pointed or sharpened surfaces that can rupture the inflation balloon. The anastomosis device can include a reinforced or otherwise protected inflation balloon to resist puncturing by a bladder retention structure. The anastomosis device can include a catheter wall profile selected to physically prevent bladder retention structures from being forcibly bent back so as to avoid potential contact with and puncture of the inflation balloon. The anastomosis device can include a catheter funnel with an internal spring for preventing kinking of the catheter lumen while providing for flexibility and stretch of the funnel to absorb pulling or shock force which can rupture the inflation balloon.

7 Claims, 12 Drawing Sheets

U.S. PATENT DOCUMENTS

| | | | |
|---|---|---|---|
| 5,123,908 A | 6/1992 | Chen | |
| 5,152,772 A | 10/1992 | Sewell, Jr. | |
| 5,306,226 A | 4/1994 | Salama | |
| 5,540,701 A * | 7/1996 | Sharkey et al. | 606/153 |
| 5,545,171 A | 8/1996 | Sharkey et al. | |
| 5,695,504 A | 12/1997 | Gifford, III et al. | |
| 5,707,380 A | 1/1998 | Hinchliffe et al. | |
| 5,833,698 A | 11/1998 | Hinchliffe et al. | |
| 5,931,842 A | 8/1999 | Goldsteen et al. | |
| 5,964,791 A | 10/1999 | Bolmsjo | |
| 6,024,748 A | 2/2000 | Manzo et al. | |
| 6,119,045 A | 9/2000 | Bolmsjo | |
| 6,149,667 A | 11/2000 | Hovland et al. | |
| 6,193,734 B1 | 2/2001 | Bolduc et al. | |
| 6,238,368 B1 | 5/2001 | Devonec | |
| 6,254,570 B1 | 7/2001 | Rutner et al. | |
| 6,299,598 B1 | 10/2001 | Bander | |
| 6,302,905 B1 | 10/2001 | Goldsteen et al. | |
| 6,391,039 B1 | 5/2002 | Nicholas et al. | |
| 6,416,545 B1 | 7/2002 | Mikus et al. | |
| 6,440,146 B2 | 8/2002 | Nicholas et al. | |
| 6,447,533 B1 | 9/2002 | Adams | |
| 6,461,367 B1 | 10/2002 | Kirsch et al. | |
| 6,485,496 B1 | 11/2002 | Suyker et al. | |
| 6,494,908 B1 | 12/2002 | Huxel et al. | |
| 6,520,974 B2 | 2/2003 | Tanner et al. | |
| 6,530,932 B1 | 3/2003 | Swayze et al. | |
| 6,562,024 B2 | 5/2003 | Alvarez de Toledo et al. | |
| 6,565,579 B2 | 5/2003 | Kirsch et al. | |
| 6,599,311 B1 | 7/2003 | Biggs et al. | |
| 6,602,243 B2 | 8/2003 | Noda | |
| 6,695,832 B2 | 2/2004 | Schon et al. | |
| 6,702,825 B2 | 3/2004 | Frazier et al. | |
| 6,719,709 B2 | 4/2004 | Whalen et al. | |
| 6,719,749 B1 | 4/2004 | Schweikert et al. | |
| 6,726,697 B2 | 4/2004 | Nicholas et al. | |
| 6,740,098 B2 | 5/2004 | Abrams et al. | |
| 6,746,456 B2 | 6/2004 | Xiao | |
| 6,746,472 B2 | 6/2004 | Frazier et al. | |
| 7,029,482 B1 * | 4/2006 | Vargas et al. | 606/153 |
| 2001/0049492 A1 | 12/2001 | Frazier et al. | |
| 2002/0002363 A1 | 1/2002 | Urakawa et al. | |
| 2002/0087176 A1 | 7/2002 | Greenhalgh | |
| 2003/0069629 A1 | 4/2003 | Jadhav et al. | |
| 2003/0208183 A1 | 11/2003 | Whalen et al. | |
| 2003/0229364 A1 | 12/2003 | Seiba | |
| 2004/0078047 A1 | 4/2004 | Nicholas et al. | |
| 2004/0087995 A1 | 5/2004 | Copa et al. | |
| 2005/0038470 A1 * | 2/2005 | van der Burg et al. | 606/213 |
| 2005/0070938 A1 | 3/2005 | Copa et al. | |
| 2005/0131431 A1 | 6/2005 | Copa et al. | |
| 2006/0200178 A1 * | 9/2006 | Hamel et al. | 606/153 |
| 2006/0206122 A1 | 9/2006 | Copa et al. | |
| 2006/0264985 A1 | 11/2006 | Copa et al. | |
| 2006/0276811 A1 | 12/2006 | Copa et al. | |
| 2007/0219584 A1 | 9/2007 | Copa et al. | |

FOREIGN PATENT DOCUMENTS

| | | |
|---|---|---|
| WO | WO 96/07447 | 3/1996 |
| WO | WO 99/16359 | 4/1999 |
| WO | WO 99/21490 | 5/1999 |
| WO | WO 99/21491 | 5/1999 |
| WO | WO 99/58081 | 11/1999 |
| WO | WO 2004/000135 | 12/2003 |
| WO | WO 2004/000136 | 12/2003 |
| WO | WO 2004/000137 | 12/2003 |
| WO | WO 2004/000138 | 12/2003 |
| WO | WO 2004/034913 | 4/2004 |

OTHER PUBLICATIONS

Acconcia et al., "Sutureless" Vesicourethral Anastomosis in Radical Retropubic Prostatectomy, The American Journal of Urology Review, vol. 1, No. 2, pp. 93-96 (Mar./Apr. 2003).

Hruby, G.W., "Comparison of a Novel Tissue Apposing Device and Standard Anastomotic Technique for Vesicourethral Anastomses," Journal of Endourology, vol. 20, Supplement 1 VP12-02, p. A69 (abstract) Aug. 2006.

Hruby, G.W., "Comparison of a Novel Tissue Apposing Device and Standard Anastomotic Technique for Vesicourethral Anastomses," Journal of Urology, vol. 175, No. 4, p. 347, Apr. 2006.

* cited by examiner

Prior Art

Fig. 3

Prior Art

ANASTOMOSIS DEVICE HAVING IMPROVED SAFETY FEATURES

PRIORITY CLAIM

The present application claims priority to U.S. Provisional Application Ser. No. 60/829,803, filed Oct. 17, 2006 and entitled "VARIATIONS ON ANASTOMOSIS DEVICE", which is herein incorporated by reference in its entirety.

FIELD OF THE DISCLOSURE

The invention relates generally to anastomosis devices and their associated methods of use in reconnecting tissue. More particularly, the present application is directed to improved anastomosis device designs in which complications as a result of inflation balloon puncture or device kinking can be avoided.

BACKGROUND OF THE DISCLOSURE

Anastomosis procedures are required for connecting or re-connecting certain body tissues, e.g., as part of a surgical procedure. Typically, these tissues define a body lumen such as a blood vessel, intestinal, digestive or urinary tissue that are severed and/or reconnected as part of a successful treatment. One representative example can include a radical prostatectomy procedure in which, a surgeon removes all or most of a patient's prostate. The procedure generally leaves a severed urethral stump and a severed bladder neck, which must be reconnected to so as to restore proper urinary functions.

A representative procedure describing the use of an anastomosis device in connecting a severed urethral stump and a severed bladder neck is described in U.S. Patent Publication No. 2005/0070938A1, which is commonly assigned to the assignee of the present application, American Medical Systems of Minnetonka, Minn. Through the use of a combination of retention features including an inflation balloon and a plurality of tissue approximating structures described as extendable tines, the urethral stump and bladder neck can be aligned and retained in contact throughout a healing period for the tissue. While the urethral stump and bladder neck forcibly hold the tissue during healing, the anastomosis device provides a drainage lumen allowing bodily fluids and other materials to pass during the healing period.

While the aforementioned anastomosis device effectively reconnects tissue during surgical procedures, it would be advantageous to improve upon present designs to enhance the functionality, reliability and safety associated with use of anastomosis devices.

SUMMARY OF THE DISCLOSURE

An anastomosis device of the present disclosure accomplishes the goals of providing increased functionality, reliability and safety to existing anastomosis device designs through the use of designs addressing potential puncture of an inflation balloon being used to hold and approximate tissue. In some representative embodiments, an anastomosis device of the present invention can comprise bladder retention structures configured to engage and retain tissue without pointed or sharpened surfaces that can rupture the inflation balloon. Representative bladder retention structures can comprise looped configurations, flattened or paddle-shaped configurations, conical or ball shaped configurations, twisted coil configurations and pre-formed tine configurations in which an end is pre-formed to face away from the inflation balloon. In some representative embodiments, an anastomosis device of the present invention can comprise a reinforced or otherwise protected inflation balloon to resist puncturing by a bladder retention structure. In some representative embodiments, an anastomosis device of the present invention can comprise a catheter wall profile selected to physically prevent bladder retention structures from being forcibly bent back, possibly leading to contact with and puncture of the inflation balloon. In some representative embodiments, an anastomosis device of the present invention can comprise a catheter funnel including an internal spring for preventing kinking of the catheter lumen while providing for flexibility and stretch of the funnel to absorb pulling or shock force which can rupture the inflation balloon. In certain representative embodiments, combinations of these previously identified features can be utilized to further reduce the potential for rupture of the inflation balloon.

In one aspect of the present disclosure, an anastomosis device can comprise a catheter body having a distal portion with an inflation balloon and a plurality of tissue approximation structures. Generally, the tissue approximation structures can comprise at least two distinct sets of projecting structures intended to engage and retain body tissue during a healing period. A distalmost tissue approximating structure is generally located between the inflation balloon and a proximalmost tissue approximating structure. The projecting structures on the distalmost tissue approximating structure can comprise a puncture-resistant configuration so as to avoid accidental puncture of the inflation balloon. In certain embodiments, the puncture-resistant configuration can comprise looped configurations, flattened or paddles shaped configurations, conical or ball shaped configurations, twisted coil configurations and pre-formed tine configurations in which an end is pre-formed to face away from the inflation balloon.

In another aspect of the present disclosure, an anastomosis device can again comprise a catheter body having a distal portion with an inflation balloon and a plurality of tissue approximation structures. Generally, the tissue approximation structures comprise at least two distinct sets of projecting structures intended to engage and retain body tissue during a healing period. A distalmost tissue approximating structure is generally located between the inflation balloon and a proximalmost tissue approximating structure. The catheter body can comprise a catheter wall profile selected to physically prevent the distalmost tissue approximating structure from being forcibly bent back such that potential contact of the inflation balloon with the distalmost tissue approximating structure is physically avoided.

In yet another aspect of the present disclosure, an anastomosis device comprises a catheter body having a distal portion with an inflation balloon and a plurality of tissue approximation structures. Generally, the tissue approximation structures comprise at least two distinct sets of projecting structures intended to engage and retain body tissue during a healing period. A distalmost tissue approximating structure is generally located between the inflation balloon and a proximalmost tissue approximating structure. The inflation balloon can comprise a reinforced or otherwise protected inflation balloon to resist puncturing by the distalmost tissue approximating structure. In some embodiments, the inflation balloon can comprise a reinforcement layer that covers at least a proximalmost hemisphere of the inflation balloon. In some alternative embodiments, the inflation balloon can include distinct reinforcement portions that physically correspond to the positioning of individual retention elements that define the distalmost tissue approximating structure.

In another aspect of the present disclosure, an anastomosis device comprises a catheter body having a distal portion with an inflation balloon and a plurality of tissue approximation structures as well as a proximal portion including a catheter funnel for attachment to external biasing and control devices. Generally, the catheter funnel can comprise an integrated strain relief portion to absorb external forces so as to not translate said external forces to the distal portion during a tissue healing period. The integrated strain relief generally comprises an internal string that allows for stretching of the integrated strain relief portion while simultaneously resisting twisting of the integrated strain relief to avoid kinking of the catheter funnel. By avoiding kinking, an internal catheter lumen as well as any actuatable guidewires within the catheter body remain in an operational state while at the same time, external forces that can lead to rupture and deflation of the inflation balloon or other tissue trauma can be avoided.

In yet another aspect of the present disclosure, methods for joining tissue with an anastomosis device can comprise providing an anastomosis device having an inflation balloon and a tissue approximation structure, wherein said inflation balloon is protected from potential puncture by the tissue approximation structure. In some embodiments, protecting the inflation balloon can comprise fabricating the tissue approximation structure in a puncture-resistant configuration such as, for example, forming tissue retention members in looped configurations, flattened or paddles shaped configurations, conical or ball shaped configurations, twisted coil configurations and pre-formed tine configurations in which an end is preformed to face away from the inflation balloon. In some embodiments, protecting the inflation balloon can comprise fabricating a catheter wall having a wall profile selected to physically prevent tissue retention members from being forcibly bent back such that potential puncture of the inflation balloon with the retention members is physically avoided. In some embodiments, protecting the inflation balloon can comprise fabricating the inflation balloon with a reinforcement layer that covers at least portions of a proximalmost hemisphere of the inflation balloon such that said inflation balloon is increasingly resistant to puncture by the retention members. In some embodiments, protecting the inflation balloon can comprise fabricating a proximalmost portion of a catheter body to include a catheter funnel with an internal spring capable of simultaneously absorbing external tension and forces while preventing kinking of the catheter body.

The above summary of the invention is not intended to describe each illustrated embodiment or every implementation of the present invention. The Figures and the detailed description that follow more particularly exemplify these embodiments.

BRIEF DESCRIPTION OF THE FIGURES

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE FIGURES

Figure 1:
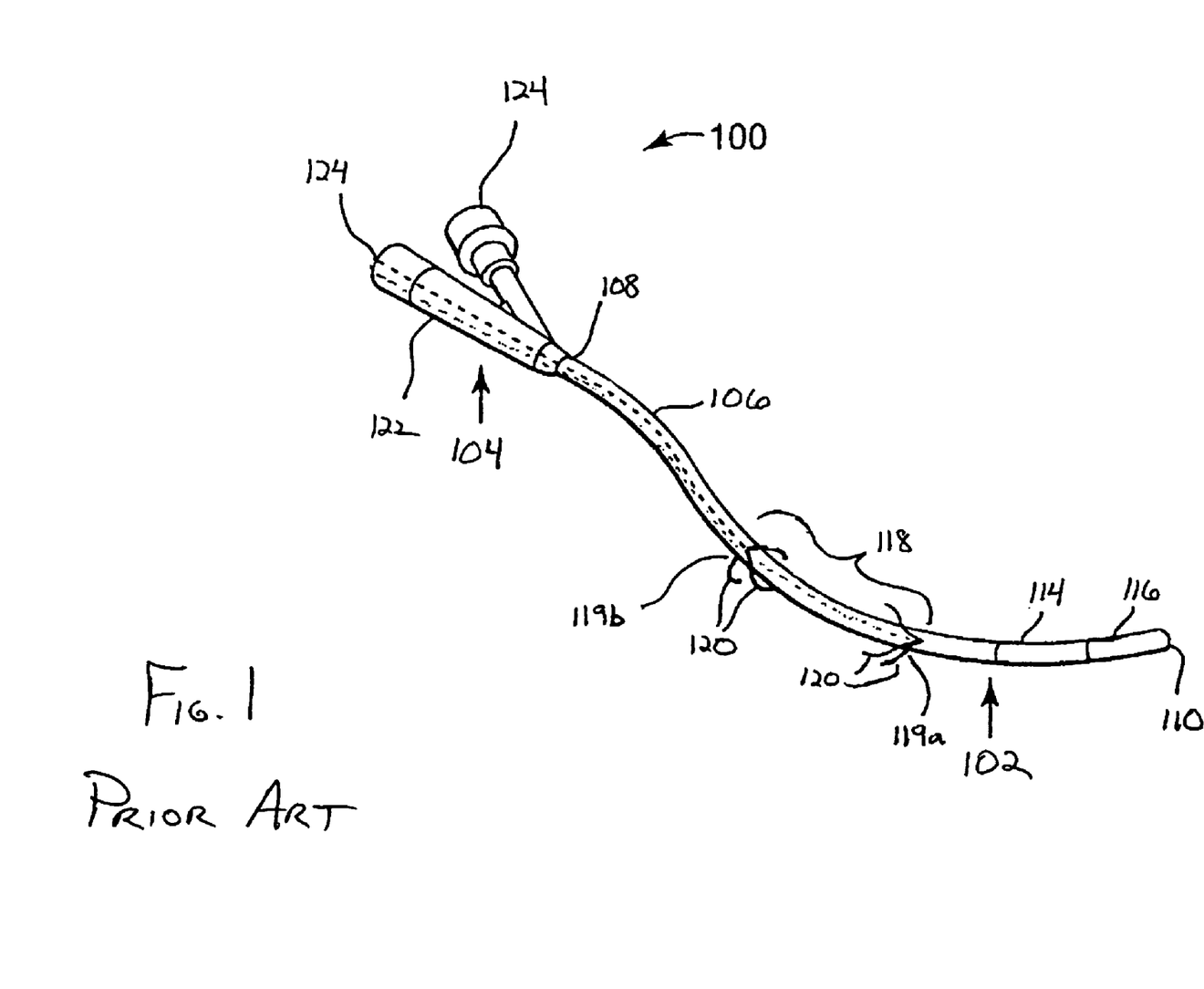
FIG. 1 is a perspective view of an anastomosis device of the prior art.
Figure 2:
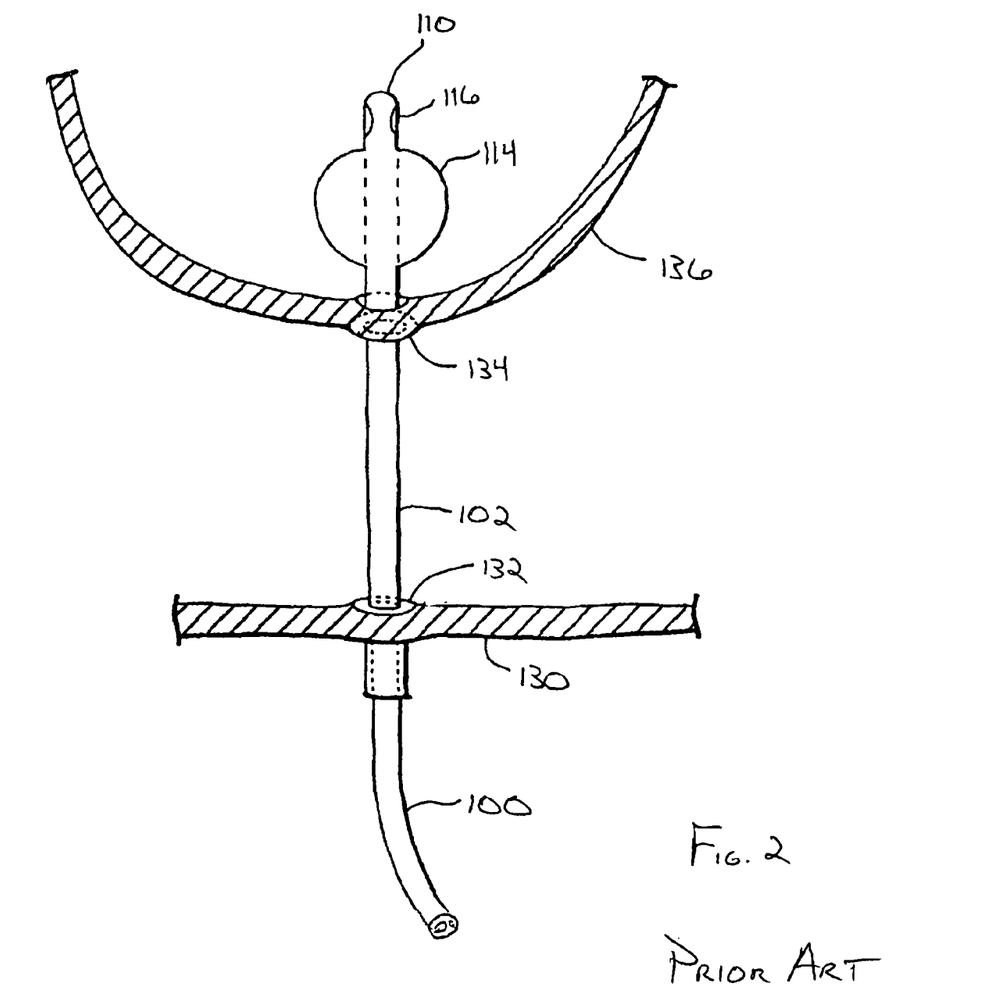
FIG. 2 is a schematic, side view of the anastomosis device of FIG. 1 as utilized in a radical prostatectomy.

Referring generally to FIGS. 1 and 2, an anastomosis device 100 of the prior art can comprise a catheter portion 102 and an actuation portion 104. Catheter portion 102 generally comprises a catheter body 106 having a proximal connection portion 108 and a distal end portion 110. Catheter body 102 is generally constructed of a soft plastic or rubber tube. Located proximate to distal end portion 110, the catheter body can include an inflation balloon 114, a drainage aperture 116 and a tissue approximating structure 118. Tissue approximating structure 118 can comprise a single structure or multiple structures generally positioned along the catheter body 106 between the distal end portion 110 and the proximal connection portion 108. Tissue approximating structure 118 can include multiple sharp elongate tines 120 that can extend from and retract into catheter body 106 at a location that allows contact and optional penetration of adjacent tissue structures. Tissue approximation structure 118 can comprise a distalmost approximating structure 119a and a proximalmost approximating structure 119b.

Referring again to FIG. 1, proximal connection portion 108 of the anastomosis device 100 can operably connect to actuation portion 104 at an actuation body 122. Actuation body 122 generally possesses an increased diameter than catheter body 106. Actuation body 122 can include one or more ports 124 that extend or otherwise protrude from the actuation body 122 and generally provide access to distinct lumens defined within the catheter body 106 that can provide for inflation of the inflation balloon 114, drainage from the drainage aperture 116 or for control guidewires to operably connect to the tissue approximating structures 118.

Figure 3:
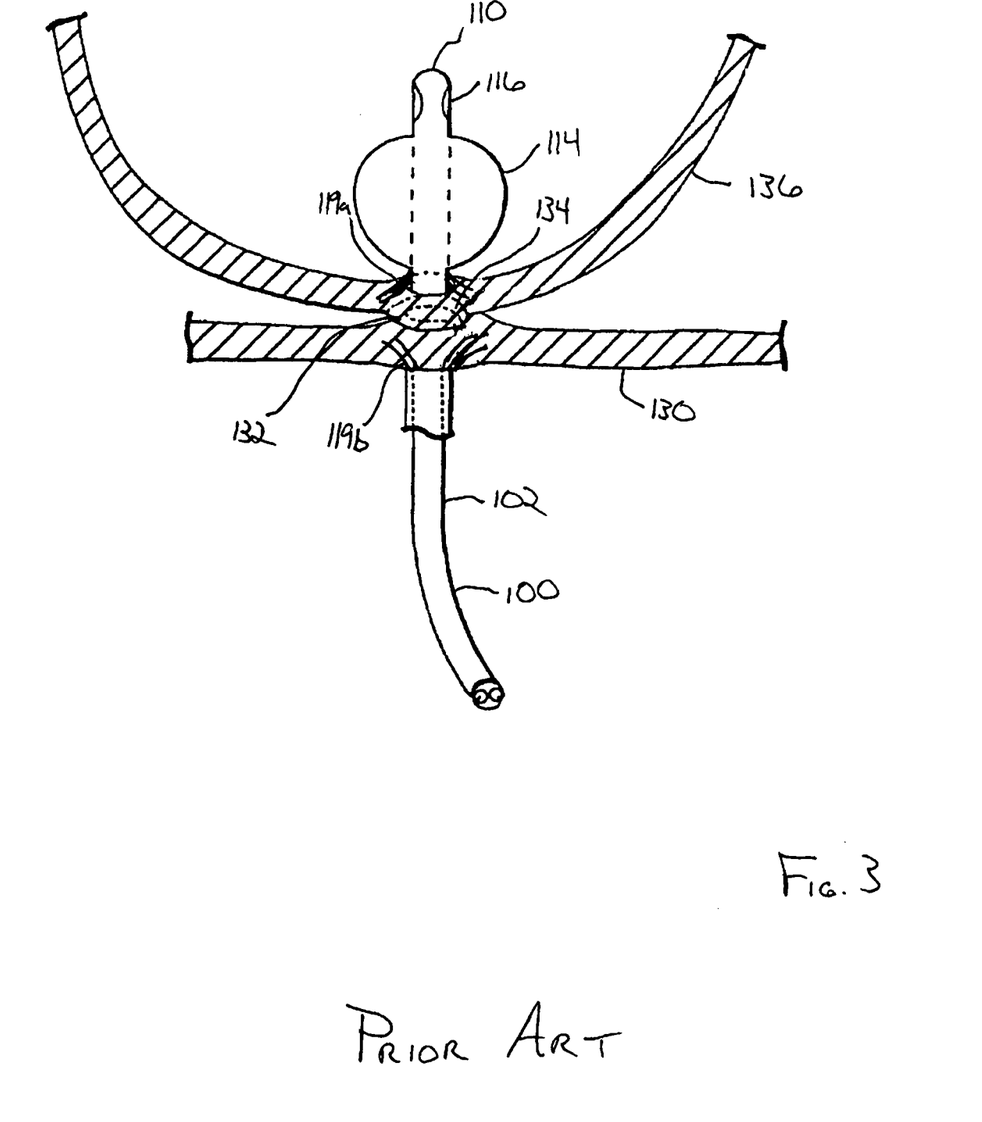
FIG. 3 is a schematic, side view of the anastomosis device of FIG. 1 as utilized in a radical prostatectomy.

Referring to FIG. 2, one representative use for anastomosis device 100 is in a radical prostatectomy in which the prostate has been surgically removed. Generally, catheter body 102 is advanced such that the distal end portion 110 is directed through perineal floor 130, urethral stump 132, bladder neck 134 and into bladder 136. With distal end portion 110 positioned within bladder 136, inflation balloon 114 is inflated such that urethral stump 132 and bladder neck 134 can be approximated by pulling on inflation balloon 114. With urethral stump 132 and bladder neck 134 in approximation, distalmost approximation structure 119a can be deployed to capture and retain the bladder neck 134 while proximalmost approximation structure 119b is deployed to capture and retain the urethral stump 132 as shown in FIG. 3. With the tissue approximation structure 118 deployed, the urethral stump 132 and bladder neck 134 are retained in contact during a healing period which, can last anywhere from 1 to 21 days or longer depending upon the procedure and tissue type.

Figure 4:
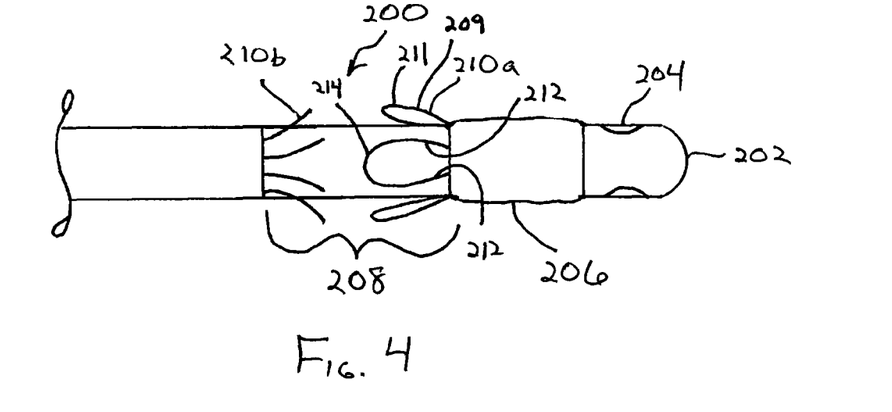
FIG. 4 is a side view of a distal portion of an anastomosis device with a deflated inflation balloon according to an embodiment of the present disclosure.
Figure 5:
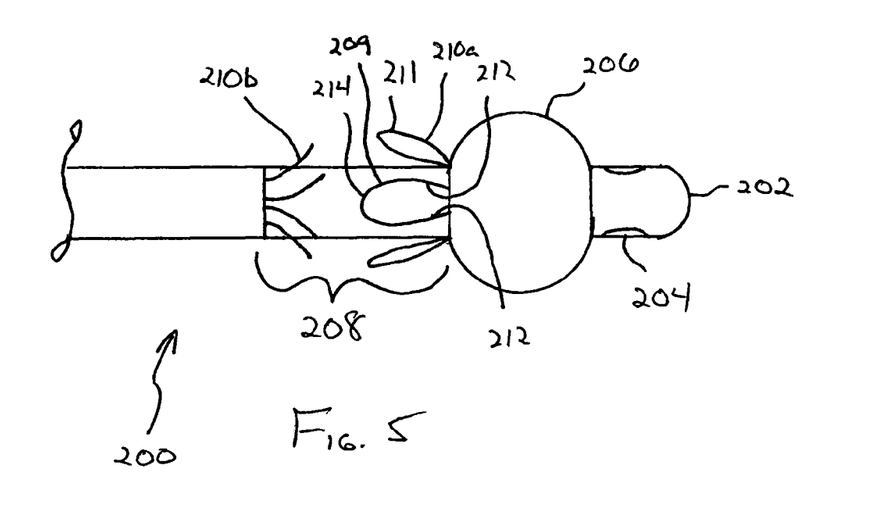
FIG. 5 is a side view of the anastomosis device of FIG. 4 with an inflated inflation balloon.

In an embodiment of anastomosis device 200 according to the present invention, improved designs for approximation structures can improve safety and help to prevent accidental/unintentional deflation of the inflation balloon as a result of puncturing by the approximation structures. Referring to FIGS. 4 and 5, anastomosis device 200 can resemble anastomosis device 100 in both appearance and operation with the exception of changes at distal end portion 202. Generally, distal end portion 202 can comprise a drainage lumen 204, an inflation balloon 206 and a tissue approximation structure 208. Tissue approximation structure 208 generally comprises a distalmost approximation structure 210a and a proximalmost approximation structure 210b. Distalmost approximation structure 210a can comprise a puncture resistant configuration 209 defined by a loop structure 211 having a pair of leg portions 212 and an arcuate tissue engagement portion 214.

Anastomosis device 200 can be utilized as previously described with respect to anastomosis device 100 in FIGS. 2 and 3. As urethral stump 132 and bladder neck 134 are approximated, distalmost approximation structure 210a is deployed such that arcuate tissue engagement portion 214 engages bladder neck 134. In the event that external forces or pressure are applied to anastomosis device 200, either during initial tissue capture or during the healing period, inflation balloon 206 is in no danger of puncture by the distalmost approximation structure 210a as there are no sharpened tips or edges on arcuate tissue engagement portion 214 capable of perforating the inflation balloon 206.

Figure 6:
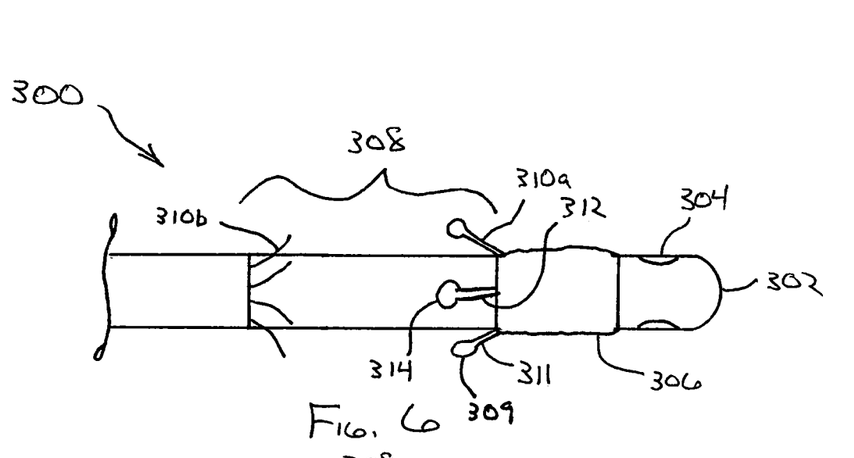
FIG. 6 is a side view of a distal portion of an anastomosis device with a deflated inflation balloon according to an embodiment of the present disclosure.
Figure 7:
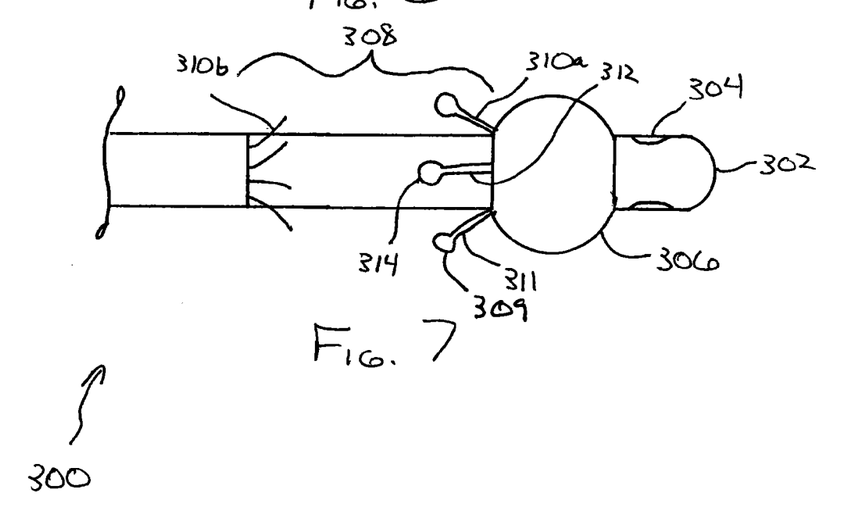
FIG. 7 is a side view of the anastomosis device of FIG. 6 with an inflated inflation balloon.

In another embodiment illustrated in FIGS. 6 and 7, an anastomosis device 300 can resemble anastomosis device 100 in both appearance and operation with the exception of changes at distal end portion 302. Generally, distal end portion 302 can comprise a drainage lumen 304, an inflation balloon 306 and a tissue approximation structure 308. Tissue approximation structure 308 generally comprises a distalmost approximation structure 310a and a proximalmost approximation structure 310b. Distalmost approximation structure 310a can comprise a puncture resistant configuration 309 defined by a rounded structure 311 having a leg portion 312 and a ball tissue engagement portion 314.

Anastomosis device 300 can be utilized as previously described with respect to anastomosis device 100 in FIGS. 2 and 3. As urethral stump 132 and bladder neck 134 are approximated, distalmost approximation structure 310a is deployed such that ball tissue engagement portion 314 engages bladder neck 134. In the event that external forces or pressure are applied to anastomosis device 300, either during initial tissue capture or during the healing period, inflation balloon 306 is in no danger of puncture by the distalmost approximation structure 310a as there are no sharpened tips or edges on ball tissue engagement portion 314 capable of perforating the inflation balloon 306.

Figure 8:
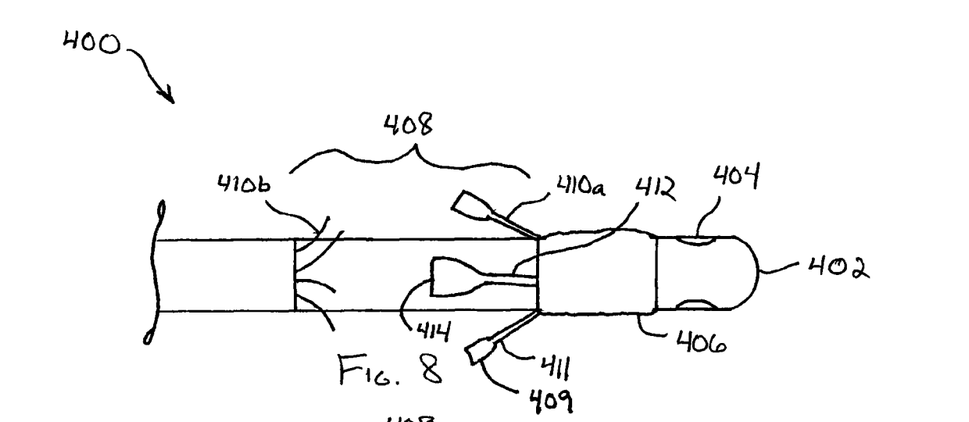
FIG. 8 is a side view of a distal portion of an anastomosis device with a deflated inflation balloon according to an embodiment of the present disclosure.
Figure 9:
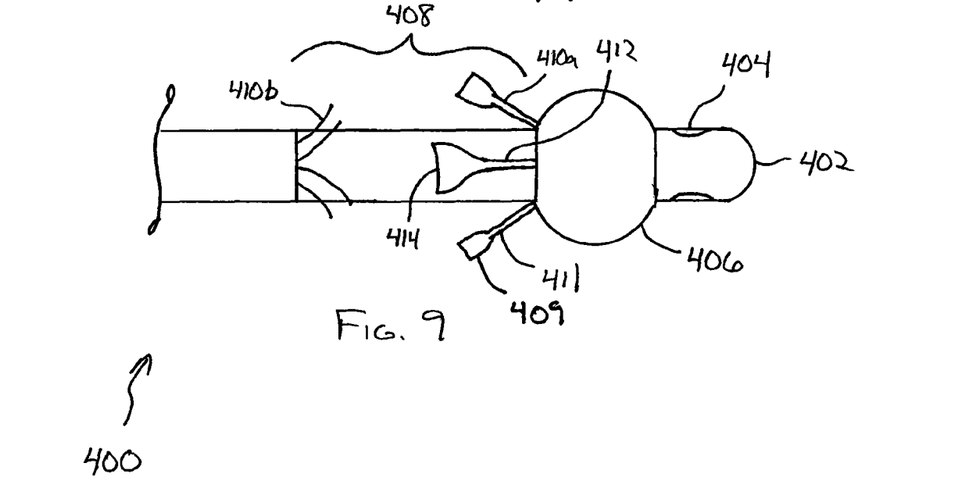
FIG. 9 is a side view of the anastomosis device of FIG. 8 with an inflated inflation balloon.

In another embodiment illustrated in FIGS. 8 and 9, an anastomosis device 400 can resemble anastomosis device 100 in both appearance and operation with the exception of changes at distal end portion 402. Generally, distal end portion 402 can comprise a drainage lumen 404, an inflation balloon 406 and a tissue approximation structure 408. Tissue approximation structure 408 generally comprises a distalmost approximation structure 410a and a proximalmost approximation structure 410b. Distalmost approximation structure 410a can comprise a puncture resistant configuration 409 defined by a paddle structure 411 having a leg portion 412 and a flattened tissue engagement portion 414.

Anastomosis device 400 can be utilized as previously described with respect to anastomosis device 100 in FIGS. 2 and 3. As urethral stump 132 and bladder neck 134 are approximated, distalmost approximation structure 410a is deployed such that flattened tissue engagement portion 414 engages bladder neck 134. In the event that external forces or pressure are applied to anastomosis device 400, either during initial tissue capture or during the healing period, inflation balloon 406 is in no danger of puncture by the distalmost approximation structure 410a as there are no sharpened tips or edges on flattened tissue engagement portion 414 capable of perforating the inflation balloon 406.

Figure 10:
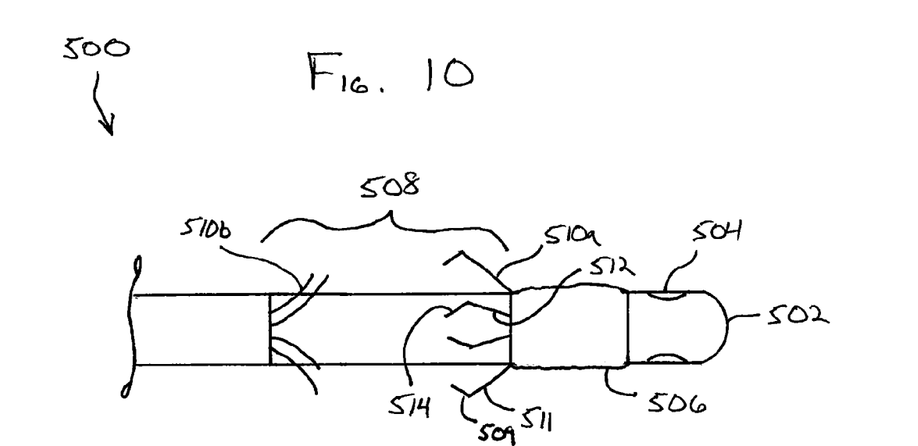
FIG. 10 is a side view of a distal portion of an anastomosis device with a deflated inflation balloon according to an embodiment of the present disclosure.
Figure 11:
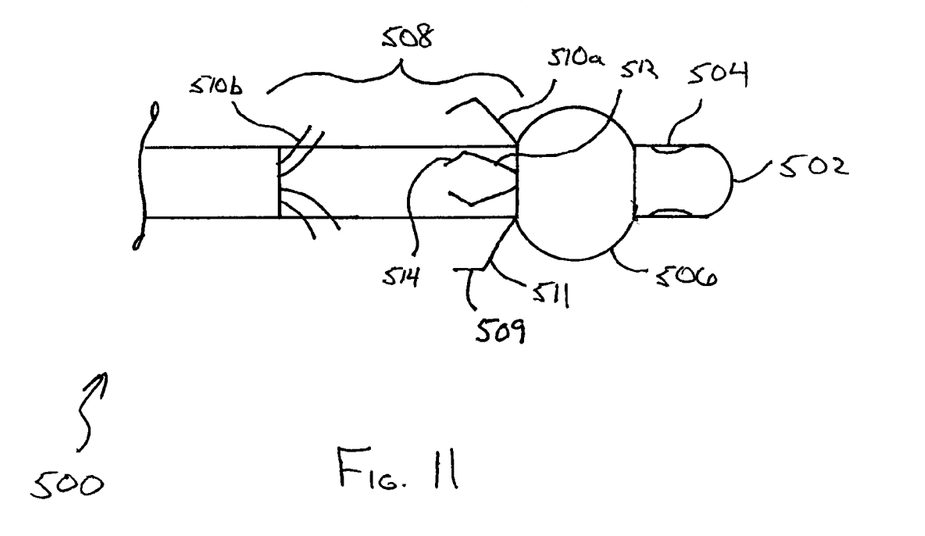
FIG. 11 is a side view of the anastomosis device of FIG. 10 with an inflated inflation balloon.

In another embodiment illustrated in FIGS. 10 and 11, an anastomosis device 500 can resemble anastomosis device 100 in both appearance and operation with the exception of changes at distal end portion 502. Generally, distal end portion 502 can comprise a drainage lumen 504, an inflation balloon 506 and a tissue approximation structure 508. Tissue approximation structure 508 generally comprises a distalmost approximation structure 510a and a proximalmost approximation structure 510b. Distalmost approximation structure 510a can comprise a puncture resistant configuration 509 defined by a preformed tine structure 511 having a leg portion 512 and an angled tissue engagement portion 514.

Anastomosis device 500 can be utilized as previously described with respect to anastomosis device 100 in FIGS. 2 and 3. As urethral stump 132 and bladder neck 134 are approximated, distalmost approximation structure 510a is deployed such that angled tissue engagement portion 514 engages bladder neck 134. In the event that external forces or pressure are applied to anastomosis device 500, either during initial tissue capture or during the healing period, inflation balloon 506 is in no danger of puncture by the distalmost approximation structure 510a as the angled nature of angled tissue engagement portion 514 prevents perforation of inflation balloon 506 even if leg portion 512 is deformed or otherwise bent toward inflation balloon 506.

Figure 12:
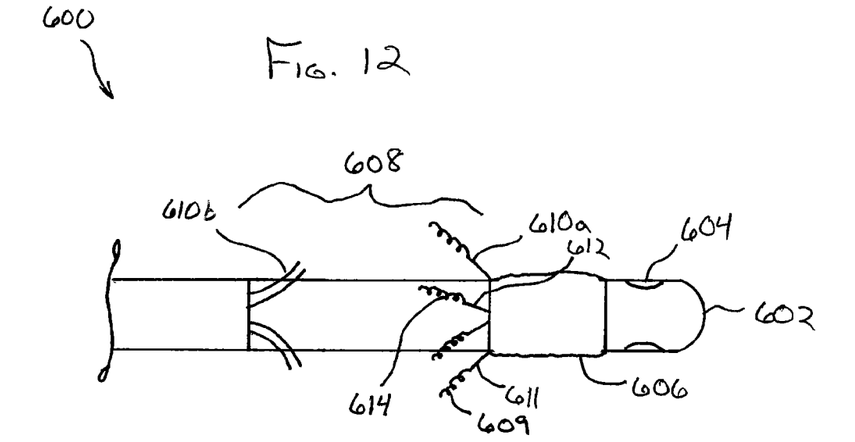
FIG. 12 is a side view of a distal portion of an anastomosis device with a deflated inflation balloon according to an embodiment of the present disclosure.
Figure 13:
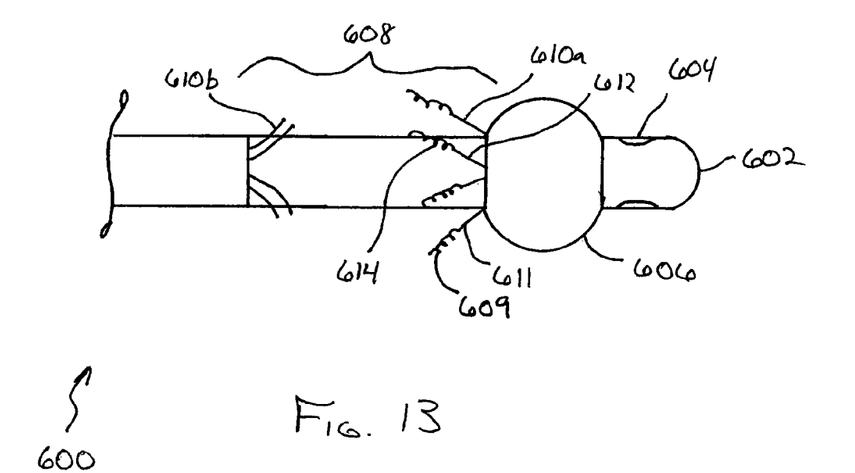
FIG. 13 is a side view of the anastomosis device of FIG. 12 with an inflated inflation balloon.

In another embodiment illustrated in FIGS. 12 and 13, an anastomosis device 600 can resemble anastomosis device 100 in both appearance and operation with the exception of changes at distal end portion 602. Generally, distal end portion 602 can comprise a drainage lumen 604, an inflation balloon 606 and a tissue approximation structure 608. Tissue approximation structure 608 generally comprises a distalmost approximation structure 610a and a proximalmost approximation structure 610b. Distalmost approximation structure 610a can comprise a puncture resistant configuration 609 defined by a coil structure 611 having a leg portion 612 and a twisted tissue engagement portion 614.

Anastomosis device 600 can be utilized as previously described with respect to anastomosis device 100 in FIGS. 2 and 3. As urethral stump 132 and bladder neck 134 are approximated, distalmost approximation structure 610a is deployed such that twisted tissue engagement portion 614 engages bladder neck 134. In the event that external forces or pressure are applied to anastomosis device 600, either during initial tissue capture or during the healing period, inflation balloon 606 is in no danger of puncture by the distalmost approximation structure 610a as there are no sharpened tips or edges on twisted tissue engagement portion 614 capable of perforating the inflation balloon 606.

Figure 14:
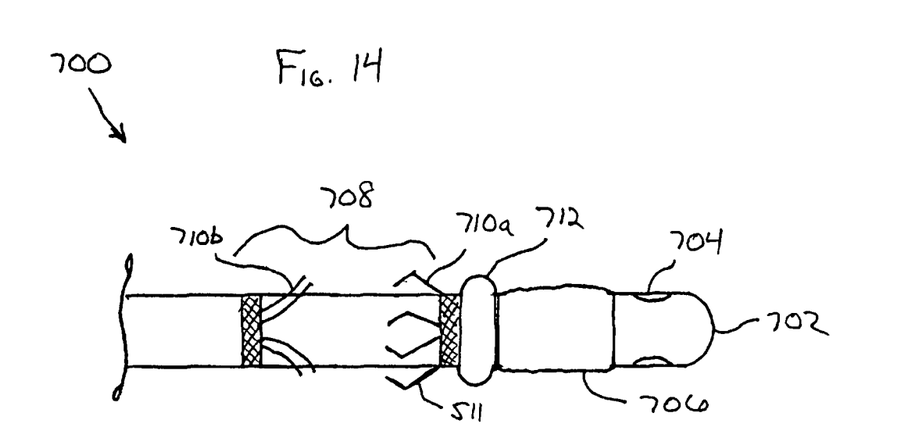
FIG. 14 is a side view of a distal portion of an anastomosis device with a deflated inflation balloon according to an embodiment of the present disclosure.
Figure 15:
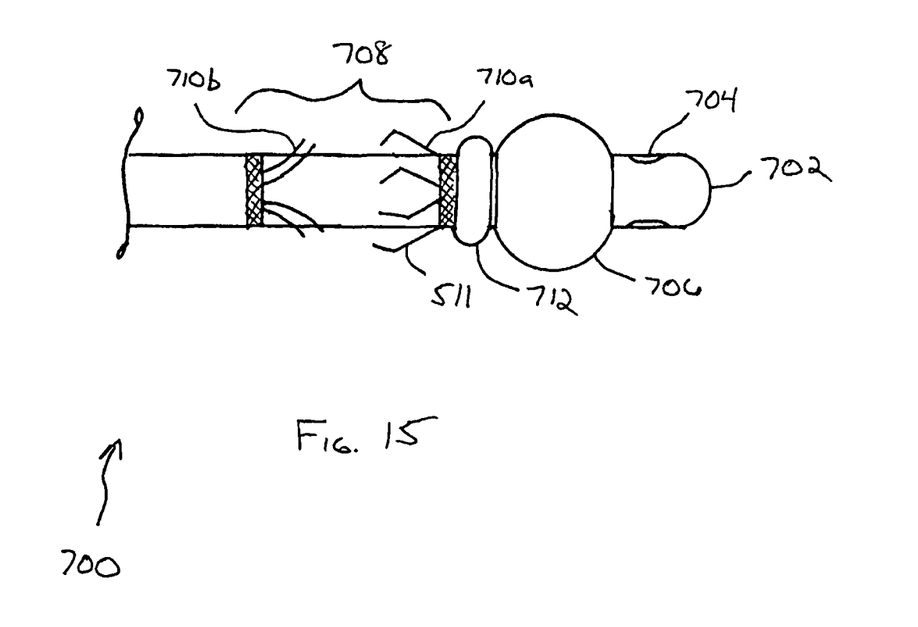
FIG. 15 is a side view of the anastomosis device of FIG. 14 with an inflated inflation balloon.

In another alternative embodiment illustrated in FIGS. 14 and 15, an anastomosis device 700 can resemble anastomosis device 100 in both appearance and operation with the exception of changes at distal end portion 702. Generally, distal end portion 702 can comprise a drainage lumen 704, an inflation balloon 706 and a tissue approximation structure 708. Tissue approximation structure 708 generally comprises a distalmost approximation structure 710a and a proximalmost approximation structure 710b. Distalmost approximation structure 710a is illustrated generally as preformed tine structure 511, though it will be understood that distalmost approximation structure can comprise any of the previously disclosed embodiments including, for example, the tines illustrated in FIGS. 1 and 3, loop structure 211, rounded structure 311, paddle structure 411 and a coil structure 611. Anastomosis device 700 can further comprise a raised profile portion 712 positioned between the distalmost approximation structure 710a and inflation balloon 706. Raised profile portion 712 can be fabricated integrally with the catheter body or can comprise a coating or molding formed over the catheter body.

Anastomosis device 700 can be utilized as previously described with respect to anastomosis device 100 in FIGS. 2 and 3. As urethral stump 132 and bladder neck 134 are approximated, distalmost approximation structure 710a is deployed such that preformed tine structure 511 engages bladder neck 134. In the event that external forces or pressure are applied to anastomosis device 700, either during initial tissue capture or during the healing period, inflation balloon 706 is in no danger of puncture by the distalmost approximation structure 710a as raised profile portion 712 physically prevents the distalmost approximation structure 710a from being capable of being bent backwards into the inflation balloon 706.

Figure 16:
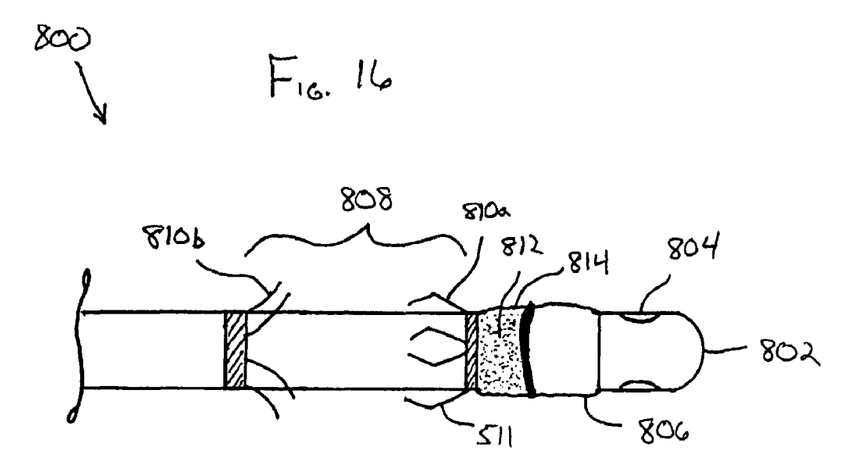
FIG. 16 is a side view of a distal portion of an anastomosis device with a deflated inflation balloon according to an embodiment of the present disclosure.
Figure 17:
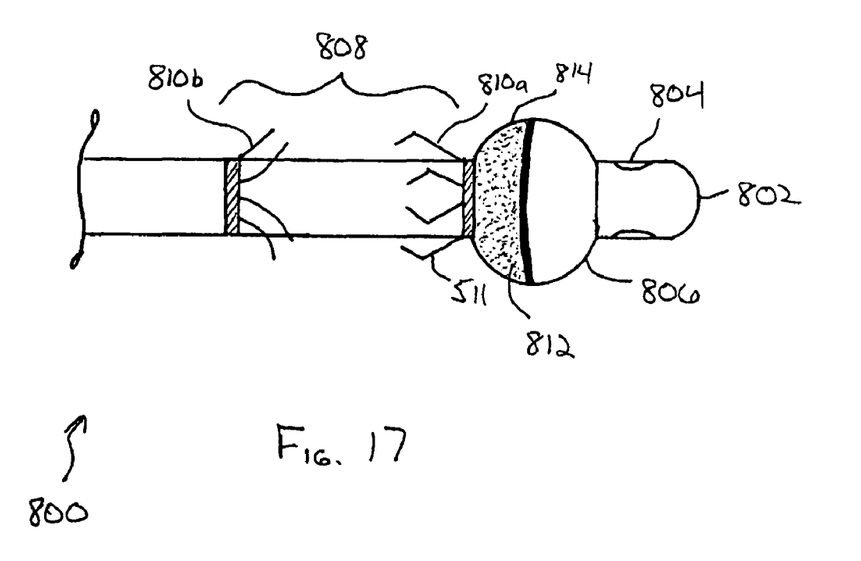
FIG. 17 is a side view of the anastomosis device of FIG. 16 with an inflated inflation balloon.

In another alternative embodiment illustrated in FIGS. 16 and 17, an anastomosis device 800 can resemble anastomosis device 100 in both appearance and operation with the exception of changes at distal end portion 802. Generally, distal end portion 802 can comprise a drainage lumen 804, an inflation balloon 806 and a tissue approximation structure 808. Tissue approximation structure 808 generally comprises a distalmost approximation structure 810a and a proximalmost approximation structure 810b. Distalmost approximation structure 810a is illustrated generally as preformed tine structure 511, though it will be understood that distalmost approximation structure 810a can comprise any of the previously disclosed embodiments including, for example, the tines illustrated in FIGS. 1 and 3, loop structure 211, rounded structure 311, paddle structure 411 and a coil structure 611. Inflation balloon 806 can be fabricated to include a protective layer 812. Protective layer 812 is located at least on a proximalmost hemisphere 814 of inflation balloon 806 such that protective layer 812 is in proximity to distalmost approximation structure 810a. In some embodiments, protective layer 812 can substantially cover all of inflation balloon 806.

Anastomosis device 800 can be utilized as previously described with respect to anastomosis device 100 in FIGS. 2 and 3. As urethral stump 132 and bladder neck 134 are approximated, distalmost approximation structure 810a is deployed such that preformed tine structure 511 engages bladder neck 134. In the event that external forces or pressure are applied to anastomosis device 800, either during initial tissue capture or during the healing period, inflation balloon 806 is protected from puncture by the distalmost approximation structure 810a as protective layer 812 provides additional strength and puncture resistance to the inflation balloon 806 in the event that approximation structure 810a was bent backwards into contact with the inflation balloon 806.

Figure 18:
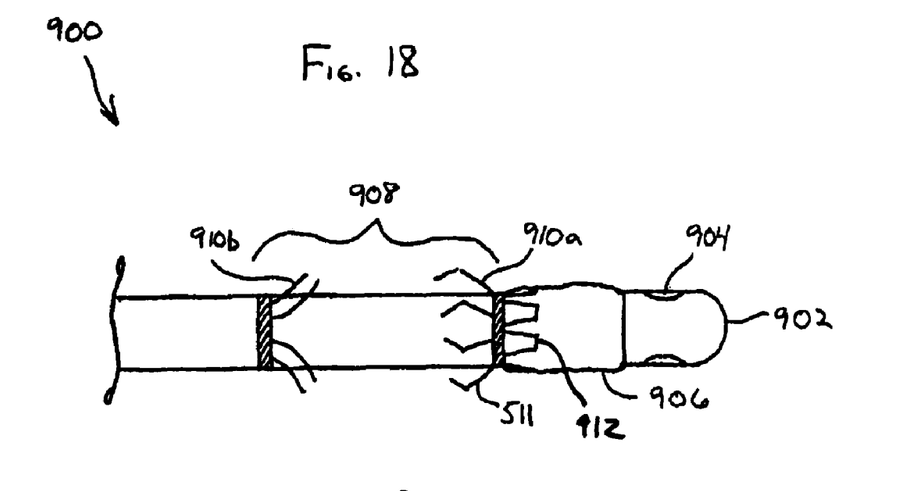
FIG. 18 is a side view of a distal portion of an anastomosis device with a deflated inflation balloon according to an embodiment of the present disclosure.
Figure 19:
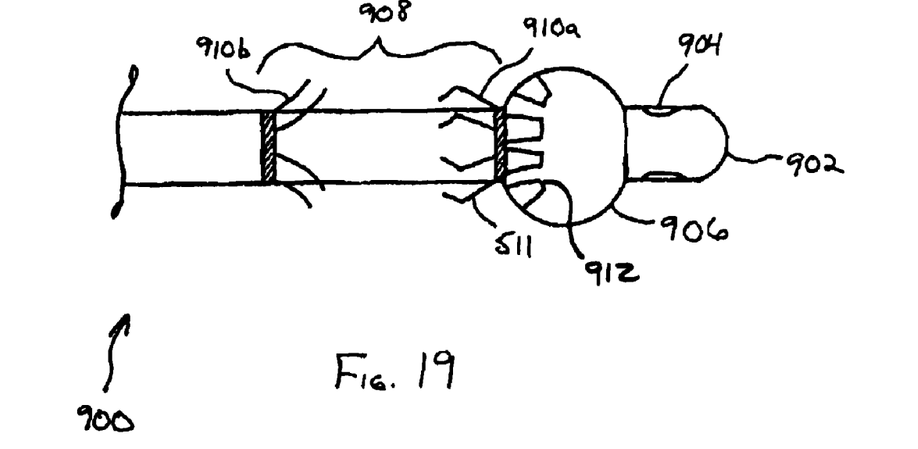
FIG. 19 is a side view of the anastomosis device of FIG. 18 with an inflated inflation balloon.

In another alternative embodiment illustrated in FIGS. 18 and 19, an anastomosis device 900 can resemble anastomosis device 100 in both appearance and operation with the exception of changes at distal end portion 902. Generally, distal end portion 902 can comprise a drainage lumen 904, an inflation balloon 906 and a tissue approximation structure 908. Tissue approximation structure 908 generally comprises a distalmost approximation structure 910a and a proximalmost approximation structure 910b. Distalmost approximation structure 910a is illustrated generally as preformed tine structure 511, though it will be understood that distalmost approximation structure 910a can comprise any of the previously disclosed embodiments including, for example, the tines illustrated in FIGS. 1 and 3, loop structure 211, rounded structure 311, paddle structure 411 and a coil structure 611. Inflation balloon 906 can be fabricated to include a plurality of protective strips 912. Protective strips 912 are spaced apart and bonded to inflation balloon 906 such that the location of each protective strip 912 corresponds to the location of each distalmost approximation structure 910a.

Anastomosis device 900 can be utilized as previously described with respect to anastomosis device 100 in FIGS. 2 and 3. As urethral stump 132 and bladder neck 134 are approximated, distalmost approximation structure 910a is deployed such that preformed tine structure 511 engages bladder neck 134. In the event that external forces or pressure are applied to anastomosis device 900, either during initial tissue capture or during the healing period, inflation balloon 906 is protected from puncture by the distalmost approximation structure 910a as the individual protective strips 912 provide additional strength and puncture resistance to the inflation balloon 906 in the event that corresponding approximation structures 910a are bent backwards into contact with the corresponding protective strip 912.

Figures 20, 21:
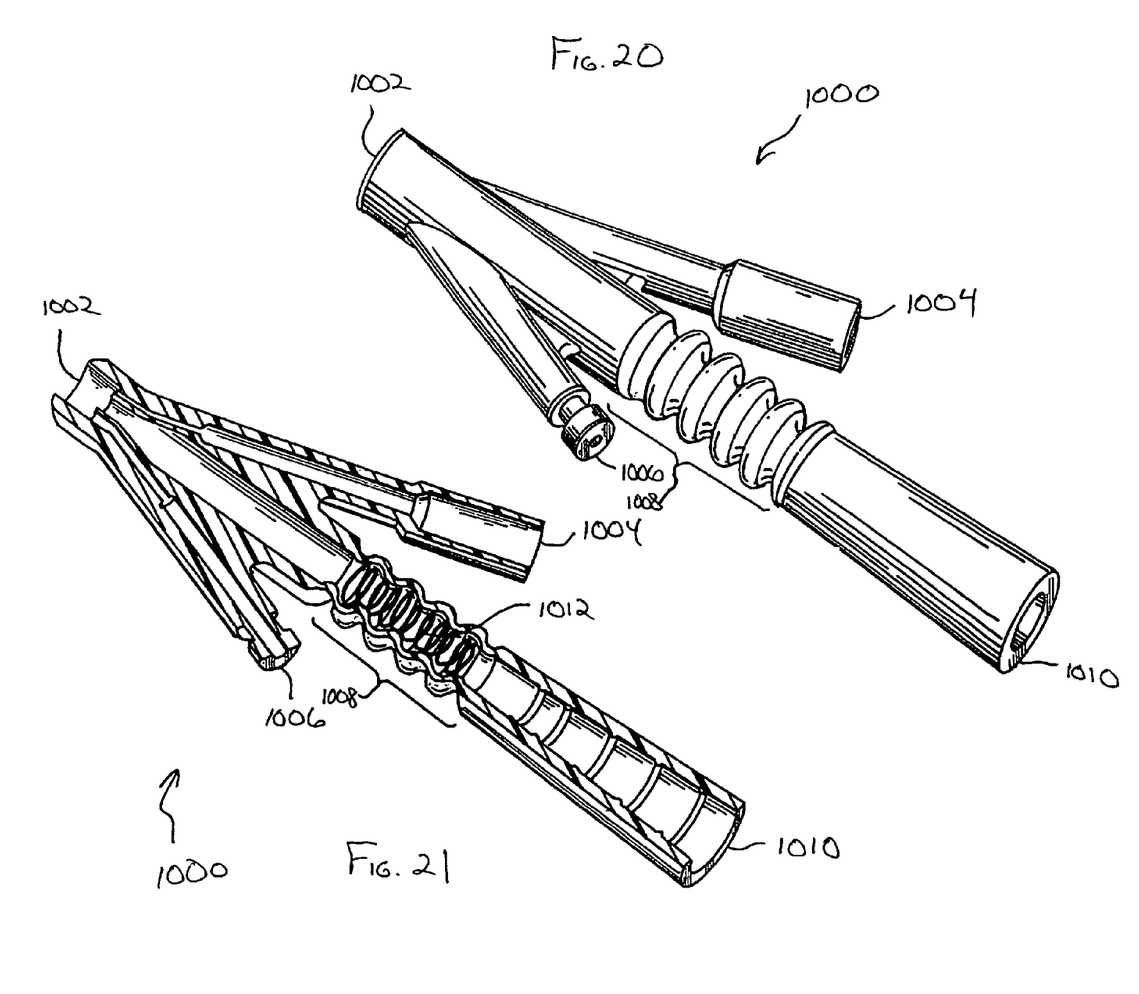
FIG. 20 is a perspective view of an actuation body according to an embodiment of the present disclosure.
FIG. 21 is a section view of the actuation body of FIG. 20.

In another embodiment of the present invention, an actuation body 1000 as illustrated in FIGS. 20 and 21 can be utilized with any of the anastomosis devices of the present invention to further protect deflation of the inflation balloon from external forces applied during the healing period. Actuation body 1000 generally comprises a distal connection portion 1002, a first port 1004, a second port 1006, a relief portion 1008 and a third port 1010. Mounted within relief portion 1008 is a relief spring 1012. Actuation body 1000 generally attaches to any of the previously disclosed anastomosis devices by coupling distal connection portion 1002 to proximal connection portion 108.

In use, a variety of devices are attached to actuation body 1000 so as to successfully operation the anastomosis device. For example, a fluid source for inflating the inflation balloon can be attached to first port 1004, a guidewire control device can be attached to second port 1006 and a drainage device can be attached to third port 1010. In the event that any forces are translated through any of these attachments, relief portion 1008, including relief spring 1012 can stretch to prevent the external force from being translated to the inflation balloon. In addition, any twisting forces applied to actuation body 1000 are resisted by relief spring 1012 to prevent kinking of relief portion 1008.

Although specific examples have been illustrated and described herein, it will be appreciated by those of ordinary skill in the art that any arrangement calculated to achieve the same purpose could be substituted for the specific example shown. This application is intended to cover adaptations or variations of the present subject matter. Therefore, it is intended that the invention be defined by the attached claims and their legal equivalents.

What is claimed:

1. An anastomosis device comprising:

A catheter body having a proximal connection portion, a distal end portion, an inflation balloon and a tissue approximating structure integral to the catheter body, the tissue approximating structure including a proximalmost approximating structure and a distalmost approximating structure the catheter body further including a raised profile portion between the inflation balloon and the distalmost approximating structure wherein the raised profile portion prevents physical contact between the inflation balloon and the distalmost approximating structure, said distalmost approximating structure having a different configuration from the proximalmost approximating structure wherein said distalmost approximating structure includes a paddle structure having a leg portion and a flattened tissue engagement portion so as to have a puncture resistant configuration when deployed from within the catheter body so as to avoid perforation of the inflation balloon when in an inflated configuration.

2. The device of claim 1, wherein the inflation balloon includes a protective element positioned proximate the distalmost approximating structure.

3. The device of claim 2, wherein the protective element includes a protective layer covering a proximalmost hemisphere of the inflation balloon.

4. The device of claim 1, further comprising an actuation body operably coupled to the proximal connection portion, the actuation body including a relief portion having an internal relief spring responding to external forces so as to prevent translation of said external forces to the catheter body.

5. An anastomosis device comprising:

a catheter body having a proximal connection portion, a distal end portion, an inflation balloon and a tissue approximating structure integral to the catheter body, the tissue approximating structure including a proximalmost approximating structure and a distalmost approximating structure wherein the inflation balloon includes a protective element positioned proximate the distalmost approximating structure, the protective element including a protective layer covering a proximalmost hemisphere of the inflation balloon, said distalmost approximating structure having a different configuration from the proximalmost approximating structure, wherein said distalmost approximating structure has a puncture resistant configuration when deployed from within the catheter body so as to avoid perforation of the inflation balloon when in an inflated configuration, and wherein an actuation body is operably coupled to the proximal connection portion, the actuation body including a relief portion having an internal relief spring responding to external forces so as to prevent translation of said external forces to the catheter body.

6. The anastomosis device of claim 5, wherein the catheter body further comprises a raised profile portion between the inflation balloon and the distalmost approximating structure and wherein the raised profile portion prevents physical contact between the inflation balloon and the distalmost approximating structure.

7. The anastomosis device of claim 5, wherein the distalmost approximating structure is selected from the group consisting essentially of: a loop structure having an arcuate tissue engagement portion, a rounded structure having a leg portion and a ball tissue engagement portion, a paddle structure having a leg portion and a flattened tissue engagement portion and a preformed tine structure having a leg portion and an angled tissue engagement portion.

* * * * *